United States Patent [19]
Gardineer et al.

[11] Patent Number: 5,373,845
[45] Date of Patent: Dec. 20, 1994

[54] APPARATUS AND METHOD FOR FORWARD LOOKING VOLUME IMAGING

[75] Inventors: Bayard Gardineer, Skillman; David Vilkomerson, Princeton, both of N.J.

[73] Assignee: Echo Cath, Ltd., Monmouth Junction, N.J.

[21] Appl. No.: 887,473

[22] Filed: May 22, 1992

[51] Int. Cl.⁵ .................................. A61B 8/12
[52] U.S. Cl. ...................... 128/660.09; 128/662.06
[58] Field of Search ............ 128/660.07, 660.09, 128/660.1, 661.07, 662.03, 662.04, 662.06, 915–916

[56] References Cited

U.S. PATENT DOCUMENTS

| | | | |
|---|---|---|---|
| 3,854,471 | 12/1974 | Wild | 128/660.09 |
| 4,757,823 | 7/1988 | Hofmeister et al. | 128/662.04 |
| 4,841,929 | 6/1989 | Dow et al. | 128/660.1 |
| 5,152,294 | 10/1992 | Mochizuki et al. | 128/660.1 X |
| 5,161,537 | 11/1992 | Hashimoto et al. | 128/661.01 X |
| 5,174,296 | 12/1992 | Watanabe et al. | 128/662.06 X |

*Primary Examiner*—Francis Jaworski
*Attorney, Agent, or Firm*—Plevy & Associates

[57] ABSTRACT

A scanning system that is forward looking that uses ultrasound for intraluminal imaging. A transducer that emits ultrasonic signals is nutatably mounted on the tip of a probe. The front mounted transducer enables intraluminal scanning of an oncoming area or volume as the probe moves to a selected position in a lumen or body cavity. Cables are used to nutate the transducer so as to provide spiral or raster scanning patterns. The cables are driven by programmable electromagnetic drives. Three dimensional images are then obtained from the reflected ultrasonic signals.

31 Claims, 9 Drawing Sheets

APPARATUS AND METHOD FOR FORWARD LOOKING VOLUME IMAGING

FIELD OF THE INVENTION

This invention relates to an ultrasonic imaging system and, more particularly, to such a system that employs an ultrasonic transducer which is mounted on a probe member to provide an ultrasonic scan of an area or volume in front of the probe.

BACKGROUND OF THE INVENTION

There are many medical procedures where imaging of blood vessels and other body lumens or internal cavities is desirable in order to ascertain the extent of plaque, stenosis, obstructions or other pathologies that may exist. A prior art technique of providing an image of a lumen employs X-ray fluoroscopy. In X-ray fluoroscopy, a contrast agent is sent through an artery of interest. The contrast agent is visible under X-ray radiation which enables an X-ray system to provide an image of the arterial obstruction. However, such X-ray imaging techniques have disadvantages. An X-ray image of an arterial obstruction is a profile of the contrast agent as it flows through the artery. Therefore, the images provided are generally of the contrast agent in a single plane of view, not of the tissue. Moreover, the true lumen diameter is generally not provided by these images. In addition, the characteristics of the plaque within the artery are not provided, which is important in determining the success of a possible angioplasty procedure. Another disadvantage is the potential harmful effects of the radiation to the patient and attending medical personnel. Furthermore, there is potential for additional harmful effects due to the contrast agent.

Other prior art imaging techniques utilize catheter technology to obtain an image of an area within a body lumen. One such system utilizes a catheter and a transducer, as shown in FIG. 1, in conjunction with an ultrasound imaging system to provide an image of an area. Ultrasonic imaging techniques are well suited for the imaging of the soft tissue found in body lumens. Moreover, ultrasonic energy is useful in the location of a catheter that has been directed into a body. In this regard, reference is made to U.S. Pat. No. 5,076,278 entitled ANNULAR ULTRASONIC TRANSDUCERS EMPLOYING CURVED SURFACES USEFUL IN CATHETER LOCALIZATION which issued on Dec. 31, 1991 to Vilkomerson et al. In addition, ultrasonic energy is not detrimental to the health or safety of attending physicians or other medical personnel.

In prior art ultrasound imaging systems, a transducer is utilized that emits an ultrasonic imaging beam. The transducer is fastened about the outside circumference of a catheter and the ultrasonic imaging beam emanates perpendicular to the catheter. Because of this, the transducer only provides an image of areas on the sides of the catheter, as shown in FIG. 1. Such prior art catheter side scanning systems generally do not provide an image of the central region of the lumen in front of the catheter tip. This is a disadvantage since it is the central region of the lumen that should be imaged in order to characterize a severe stenosis.

In addition, such prior art side scanning systems proceed blindly forward through the blood vessel as the catheter is moved. This forward, unchecked motion may inadvertently cause the catheter to contact the blood vessel wall and shear off material attached to the blood vessel wall so that it is pushed into the bloodstream. Furthermore, such prior art side scanning systems generally do not provide for the guidance of therapeutic procedures such as laser ablation or mechanical atherectomy. Moreover, prior art catheter side scanning systems provide a plane image on the side of the catheter, which prevents a substantial portion of many pathologies from being characterized.

It would be advantageous in such procedures to allow the physician or other medical personnel to view an area or volume in front of the catheter or probe tip as the catheter is moved through the lumen. In this way, the physician could view an oncoming area to anticipate an oncoming obstruction as the probe is moved to an area of interest. In addition, it would be advantageous to provide several image planes of a pathology being imaged in order to optimally characterize the pathology.

Another prior art technique utilizes a catheter that is volume imaging and front looking but does not employ ultrasonic imaging techniques. U.S. Pat. No. 4,998,916 to Hammerslag, et al discloses a steerable catheter device for coronary angioplasty applications. The device can negotiate the tortuous character of a vascular system. Fiber optic bundles are located at the tip of the device that illuminate an area in front of the device. In order to visualize a volume, a transparent inert liquid, such as a saline solution, must be discharged into the vascular system. The transparent liquid is discharged in front of the device and displaces blood from the front of the device. This enables a user to view through the liquid and observe the volume in front of the device.

However, systems employing fiber optics have disadvantages. One disadvantage is that essentially only the surfaces of the pathologies can be seen. In addition, the liquid utilized must be replaced frequently since it will dissipate and is absorbed into the vascular system. Therefore, the amount of time that this prior art device can be used is dependent upon the ability of the patient's vascular system to absorb the liquid. Moreover, this technique is not particularly reliable and is time consuming to use and therefore relatively expensive.

The present invention circumvents the drawbacks in the prior art by providing an ultrasonic scanning system that can image an area or volume in front of the probe as the probe is moved through the lumen.

SUMMARY OF THE INVENTION

A scanning system for ultrasonic imaging comprising a probe having an exploratory end and an opposite end, a transducer nutatably mounted to said exploratory end, moving means coupled to said opposite end for moving said probe to a selected position along a given path, a plurality of cables having first and second ends, wherein said transducer is coupled to said first ends, and scanning means coupled to said second ends for causing said transducer to nutate and provide a scan in front of said transducer and towards said selected position along said path.

BRIEF DESCRIPTION OF THE FIGURES

A complete understanding of the present invention may be gained by reference to the following detailed description in conjunction with the accompanying figures, in which.

DETAILED DESCRIPTION OF THE FIGURES

Figure 1:
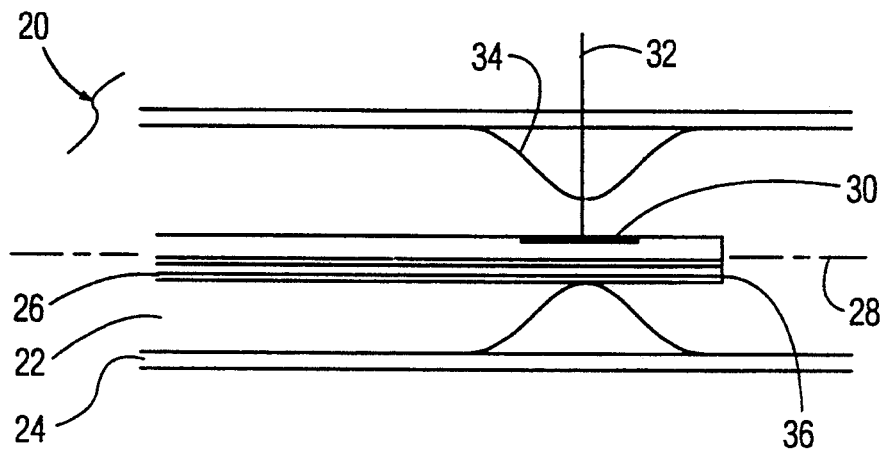
FIG. 1 shows a prior art ultrasonic side scanning system.

The above-described disadvantages of prior art ultrasonic side scanning systems will be better understood by referring to FIG. 1. In FIG. 1, a prior art ultrasonic catheter side scanning system 20 is shown positioned within a lumen 22 of a blood vessel 24. The system 20 comprises a catheter 26 having a central longitudinal axis 28. A transducer 30 is positioned on the side of the catheter 26. An imaging device (not shown) is coupled to the transducer 30 to enable the transducer 30 to emit an ultrasonic beam 32. The ultrasonic beam 32 emanates perpendicular to the central longitudinal axis 28.

In order to produce an image of an obstruction 34, the transducer 30 must be moved and rotated in the lumen 22 so that the ultrasonic beam 32 intersects the obstruction 34. The prior art side scanning system 20 provides images of obstructions that the tip 36 of the catheter 26 has already passed. Images in front of the catheter tip 36 are generally not provided by the system shown in FIG. 1.

Since the prior art side scanning system 20 does not provide an image in front of the tip 36 as the catheter 26 is advanced, the catheter 26 may contact obstructions within the blood vessel 24 or the actual wall of the blood vessel 24. Contact by the catheter 26 may dislodge a potentially harmful piece of the obstruction 34 into the blood vessel 24 or may actually damage the blood vessel 24. In addition, a plane image on the side of the catheter 26 is provided, which prevents a substantial portion of the obstruction 34 from being characterized.

Figure 2:
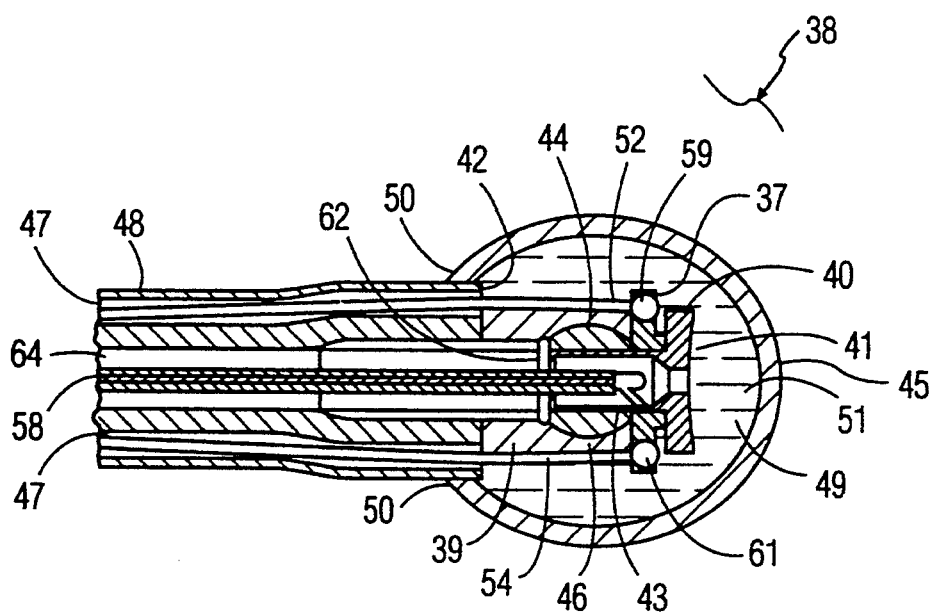
FIG. 2 depicts a present invention embodiment for an exploratory end of a probe employing three cables.

Referring now to FIG. 2, a present invention embodiment for an exploratory end 38 of a probe 48 is shown. The probe 48 may be relatively flexible in order to accommodate tortuous intravascular cavities. Alternately, the probe 48 may be substantially rigid in order to advance the probe 48 directly into a body cavity. Positioned at a forward end of the probe 48 is a transducer 40. The transducer 40 is T-shaped in a side cross section, having a forward facing concave head 41 and a rearwardly extending hollow stem 43. A cable attachment plate 37 is positioned behind the transducer 40. In addition, the plate 37 is positioned on an outside circumference of a ball 44. The stem 43 extends through the plate 37 and into the ball 44 and is affixed to the plate 37 and ball 44. The ball 44 is positioned within a socket 46, forming a ball and socket joint. The ball 44 pivots relative to the socket 46, thereby allowing the plate 37 and transducer 40 to move according to the swivel of the ball 44 within the socket 46. The socket 46 is formed in a hollow socket member 39 which is affixed to a probe tip 42.

A signal wire 58 is electrically connected to transducer 40, providing the transducer 40 with ultrasonic signals. The signal wire 58 extends through the stem 43, the socket member 39 and a central hollow 64 in the probe 48. A relief 62 is formed on the ball 44 surrounding signal wire 58, allowing the ball 44 a free range of swivel motion without contacting the signal wire 58.

A plurality of cables, each having ball shaped ends, extend through corresponding channels 47. The cables are free moving within the channels 47 and travel the length of probe 48. In the preferred embodiment, first 52, second 54 and third 56 (not shown due to side cross sectional view) cables are utilized, each having corresponding first 59, second 61 and third (not shown) ball shaped ends. The first 59, second 61 and third ball shaped ends are pivotally affixed within the plate 37, each forming ball and socket joints, which will be referred to as pivot joints. This allows the plate 37 to nutate about each pivot joint.

The movement of the plate 37 is controlled by movement of the first 52, second 54 and third 56 cables within the channels 47. Consequently, this allows the ball 44 to move within the socket 46 and thus nutate the transducer as will be explained hereinafter. In addition, the cables hold the ball 44 within the socket 46. The cables can be fabricated from a sterilizable, non-corrosive material such as stainless steel. In the preferred embodiment, the first 52, second 54 and third 56 cables are symmetrically positioned around the plate 37.

An enclosure 45 having an internal chamber 49 is positioned on the exploratory end 38 of the probe 48. The enclosure has a reversed "C" shape in a side cross section having ends 50 secured to the probe 48. The transducer 40, plate 37, ball 44, socket member 39 and forward ends of the first 52, second 54 and third 56 cables are positioned within the internal chamber 49 and are encapsulated within the enclosure 45. The internal chamber 49 is sealed and filled with a liquid 51 such as a saline solution that does not substantially affect ultrasonic energy emitted by the transducer 40 and allows the transducer 40 to nutate as previously described. In addition, the enclosure 45 may be fabricated from any suitable material such as an elastomeric material that also does not substantially affect ultrasonic energy emitted by the transducer 40. The enclosure 45 serves to protect a patient from injury that may occur due to contact of the transducer 45 or plate 37 or other element with an internal body cavity or intravascular lumen as the transducer 40 nutates. In addition, the enclosure 45 protects the above described encapsulated elements from being contaminated from blood or other bodily fluids during use.

Figure 3:
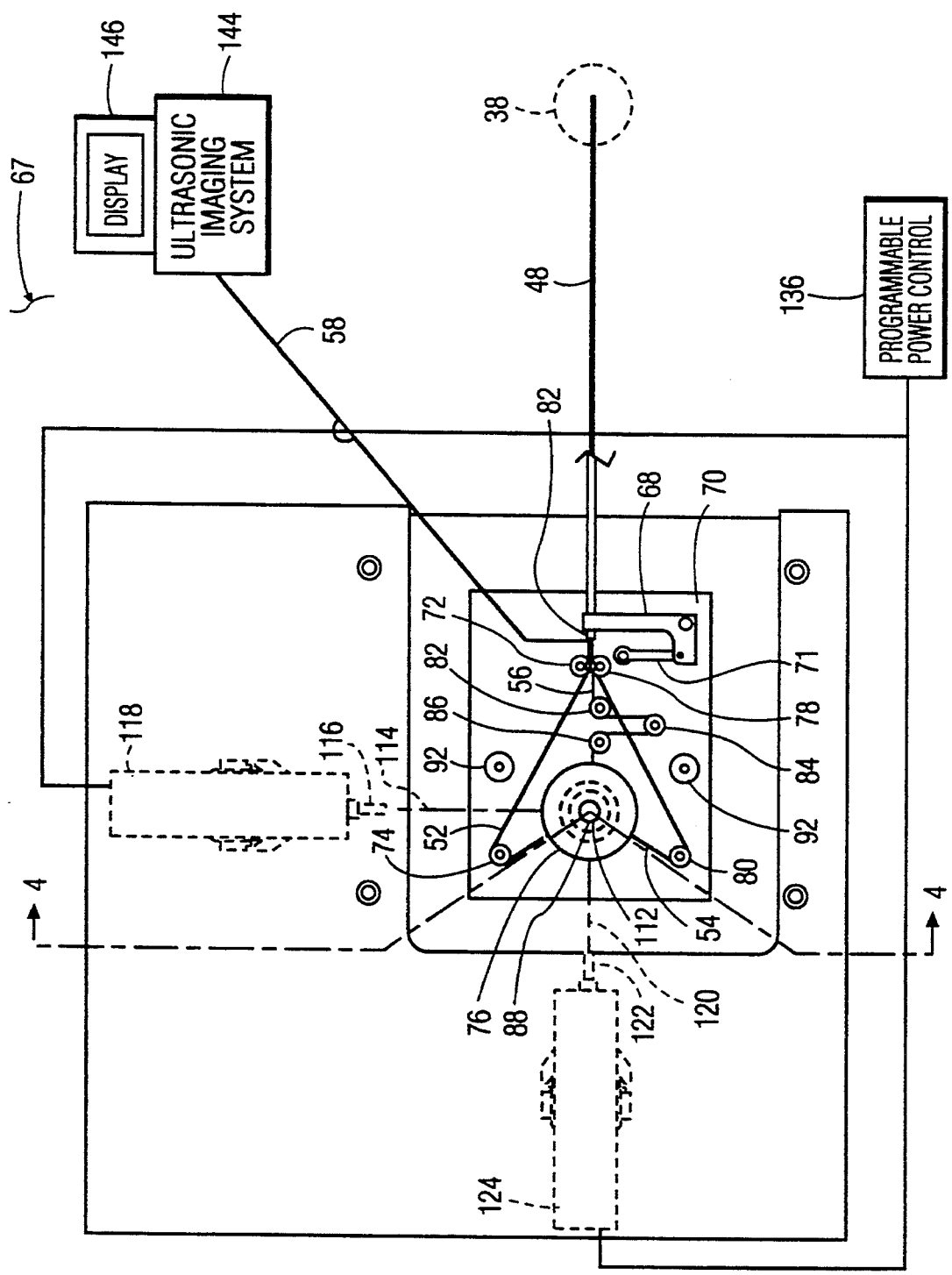
FIG. 3 is a top view of the present invention apparatus.

FIG. 3 shows a top view of the present invention apparatus 67. The exploratory end 38 of the probe 48 shown in FIG. 2 is now depicted as a smaller part of the overall scanning system. A distal end 82 of the probe 48, opposite the exploratory end 38, is fastened to the longer arm of a tension bracket 68. The tension bracket 68 is of a reversed "L" shaped configuration with a long upstanding arm and a shorter base arm and will be designated as an L shaped bracket. The L shaped bracket 68 is pivotally attached to a platform 70. The shorter arm of the L shaped bracket 68 is fastened to an end of a spring 71. An opposite end of the spring 71 is fastened to the platform 70. The spring 71 holds the L-shaped bracket 68 in a biased position.

Emerging from the distal end 82 of the probe 48 is the signal wire 58 that is electrically connected to the transducer 40 and the first 52, second 54 and third 56 cables that control the position of the transducer 40. The signal wire 58 is coupled to an ultrasonic imaging system 144 having a display 146 that produces and receives ultrasonic signals, as will later be described.

The first 52, second 54 and third 56 cables pass over a series of pulleys, positioned on the platform 70, and each cable is connected to a disc 76. The first cable 52 is passed over a first pulley 72. The first pulley 72 guides the first cable 52 to a first adjustable pulley 74. The first adjustable pulley 74 has a variable radius of rotation and is used to adjust tension in the first cable 52. The first cable 52 is then guided by the first adjustable pulley 74 to the disc 76.

The second cable 54 is passed over a second pulley 78. The second pulley 78 guides the second cable 54 to a second adjustable pulley 80. The second adjustable pulley 80 has a variable radius of rotation and is used to adjust tension in the second cable 54 in the manner previously described. The second cable 54 is then guided by the second adjustable pulley 80 to the disc 76.

The third cable 56 is passed over a third pulley 82. The third pulley 82 guides the third cable 56 to a third adjustable pulley 84. The third adjustable pulley 84 has an adjustable radius of rotation and is used to adjust tension in the third cable 56. The third adjustable 84 guides the third cable 56 to a fourth pulley 86. The third cable 56 is then passed over the fourth pulley 86 and guided to the disc 76. At the disc 76, the first 52, second 54 and third 56 cables are fastened to an outside circumference of the disc 76 in a symmetrically disposed manner, with each cable secured 120° apart from the next.

Figure 4:
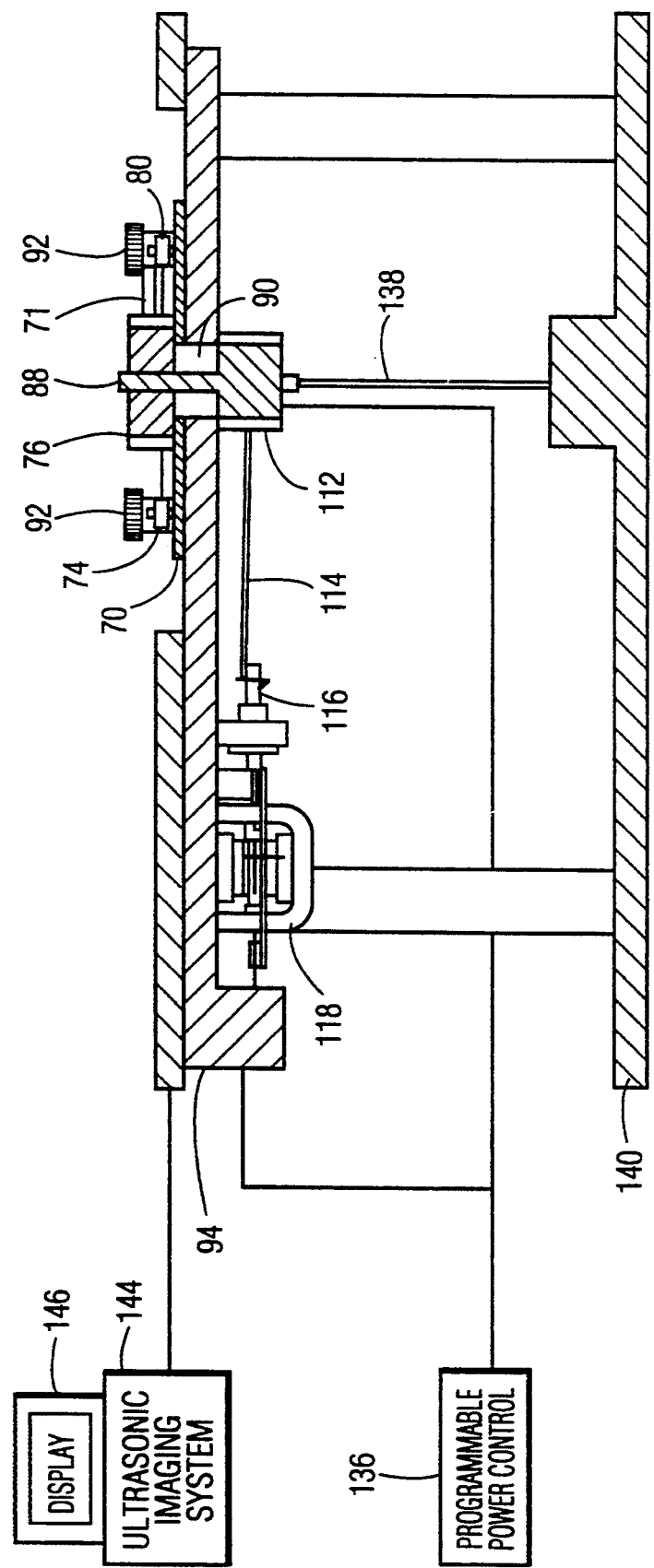
FIG. 4 is a side view along section line 4—4 of FIG. 3.

FIG. 4 is a side view of the present invention along section line 4—4 of FIG. 3. Referring to FIG. 4 in conjunction with FIG. 3, it can be seen that the disc 76 rests on the platform 70. The platform 70 is releasably secured to a main mounting element 94 by fasteners 92. An aperture 90 is formed through the main mounting element 94 and platform 70. A spindle 88 passes through the aperture 90, connecting the disc 76, positioned on top of the platform 70, to hub 112 positioned below the main mounting element 94. The spindle 88 may be unistructurally formed as part of the hub 112. However, it is preferred that the disc 76 be removable from the spindle 88 to enable the removal of the platform 70. The hub 112 is supported in place by a flexible rod 138 which is fastened to a baseplate 140. Symmetrically connected to the hub 112 are a plurality of drivewires. The drivewires are connected to a corresponding plurality of driveshafts and electromagnetic drivers.

In the shown preferred embodiment, first 114 and second 120 drivewires are used. The first 114 and second 120 drivewires extending from the hub 112 are connected to corresponding first 116 and second 122 driveshafts. The first 116 and second 122 driveshafts are driven by corresponding first 118 and second 124 electromagnetic drivers that extend and retract or vibrate the driveshafts at a desired frequency. The first 118 and second 124 electromagnetic drivers are attached to the bottom surface of the main mounting element 94. The first 118 and second 124 electromagnetic drivers are coupled to a programmable power controller 136 that controls the amplitude and frequency at which the electromagnetic drivers operate the first 116 and second 122 driveshafts and thus the first 114 and second 120 drivewires.

Since the present invention apparatus uses a transducer 40 to ultrasonically create an image, the transducer 40 must be scanned across the desired area of interest. During operation, the scanning function of the transducer 40 is ultimately controlled by the programmable power controller 136. To scan the transducer 40, a desired signal current is provided to the first 118 and second 124 electromagnetic drivers. Although any signal current can be used, the preferred signal current will cause the first 118 and second 124 electromagnetic drivers to produce sinusoidal vibrations in the first 116 and second 122 driveshafts. Additionally, it is preferred that the sinusoidal vibrations of the first 116 and second 122 driveshafts be equally out of phase with the other. For example, in the shown embodiment there are two electromagnetic drivers. As such, it is desired that the first electromagnetic drive 118 vibrate its corresponding first driveshaft 116 at a frequency 90 degrees out of phase with the second driveshaft 122. Similarly, if three electromagnetic drivers were used, it would be desirable that their corresponding driveshafts be 120 degrees out of phase.

Figure 5A:
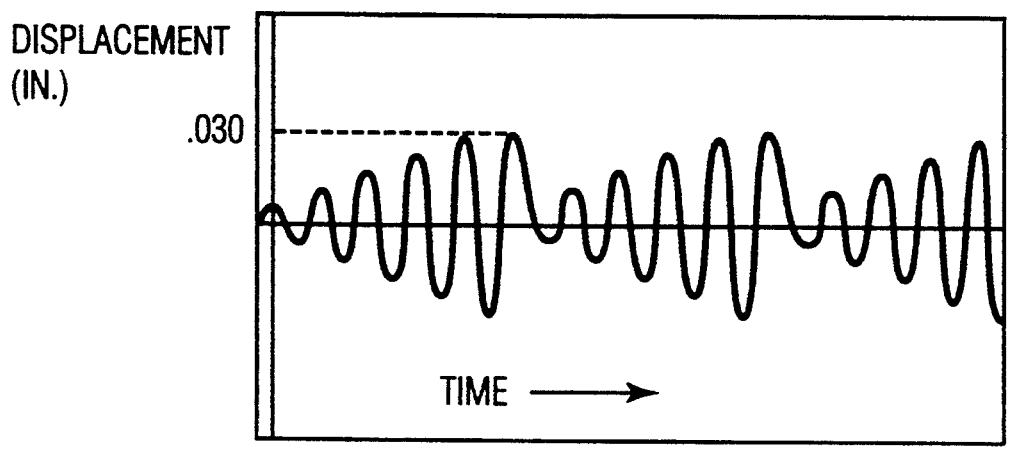
FIGS. 5A and 5B show displacements as a function of time of two driveshafts of the present invention.
Figure 5B:
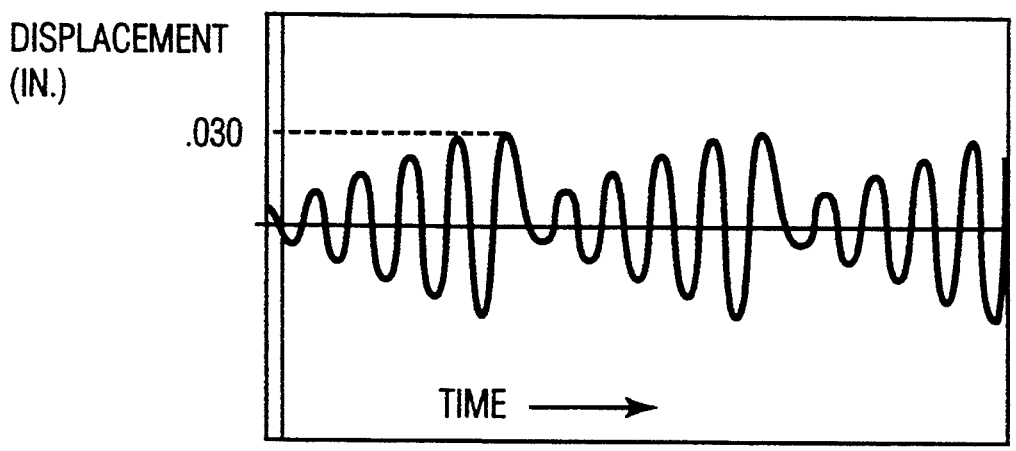

The first 118 and second 124 electromagnetic drivers vibrate the first 116 and second 122 driveshafts which produce vibrations in the first 114 and second 120 drivewires. Referring to FIGS. 5A–5B, a preferred vibration pattern is shown for each driveshaft. In FIG. 5A, a sinusoidal displacement with respect to time of the first driveshaft 116 is shown. The sinusoidal displacement begins with a minimum amplitude. The amplitude increases linearly with each sinusoidal displacement and reaches a maximum of approximately 0.030 inch. The amplitude then decreases linearly to the minimum amplitude. The frequency of the displacement motion is approximately 150 Hz. FIG. 5B shows a sinusoidal displacement with respect to time of the second driveshaft 122. As can be seen, the sinusoidal displacement of the pattern of FIG. 5B is 90 degrees out of phase with the sinusoidal displacement of the first pattern shown in FIG. 5A. The sinusoidal displacement of the second driveshaft 122 is otherwise identical to the sinusoidal displacement of the first driveshaft 116.

The sinusoidal displacement of the first 116 and second 122 driveshafts is transferred to the first 114 and second 120 drivewires. As such, the displacement of the drivewires is transferred to the hub 112. The hub 112 is supported in its nominal position by the flexible rod 138. However, since the flexible rod 138 deforms when biased, the hub 112 will move from its nominal position in accordance with the forces exerted on it by the first 114 and second 120 drivewires. The movement of the hub 112 is transferred to the disc 76 through the spindle 88. The movement of the disc 76, therefore, causes the first 52, second 54 and third 56 cables to move in a corresponding fashion. The movement of the first 52, second 54 and third cables is forward through the respective pulley arrangements into the probe 48. The first 52, second 54 and third 56 cables then cause the plate 37 to move and thus move the ball 44 to within its socket 46, causing the transducer 40 to nutate and provide a scan.

The movement of the first 52, second 54 and third 56 cables within the probe 48 may cause the probe 48 to vibrate. Since vibration of probe 48 is undesirable, the distal end 82 of the probe 48 is attached to the L shaped bracket 68. As previously described, the L shaped bracket 68 is held in a biased position by the spring 71. Vibrations in the probe 48, therefore, cause the L shaped bracket 68 to pivotally move. Consequently, the spring 71 attached to the L shaped bracket 68 is displaced and the vibrations of the probe 48 are damped.

During a medical procedure, the probe 48 and enclosure 45 are inserted into a patient's body. Consequently, the probe 48 and enclosure 45 come into contact with the patient's blood or other bodily fluids. This requires replacement of the probe 48 and enclosure 45 after use in order to maintain clean and sterilized conditions so that infections and diseases are not spread. The removability of the disc 76 and the platform 70, as previously described, enables a doctor or other medical personnel to remove the platform 70 and its elements, including the probe 48, enclosure 45, transducer 40, plate 37, associated pulleys and cables, as an entire platform assembly. The platform assembly may then be quickly replaced by another platform assembly that is sterile, enabling the doctor to proceed with another medical procedure.

Moreover, once within the patient's body, the probe 48 bends as it is continuously directed and turned in order to match a labyrinthine path of the intravascular lumen or other body cavity in which it is positioned. It is desirable to provide a scan of the volume in front of the probe tip 42 as the probe 48 bends while being moved in the intravascular lumen. As previously described, the ball 44 supporting the transducer 40 is held within its socket 46 by the tension of the first 52, second 54 and third 56 cables. Additionally, in order for the ball 44 to swivel as desired in accordance with the displacements of the first 52, second 54 and third 56 cables, there must be substantially no slack in the length of those cables. However, when the probe 48 bends as it moves along a path in a lumen, one or more of the first 52, second 54 and third 56 cables that are on the inside of the bend will lose their tension. The cable tension is substantially maintained by the L shaped bracket 68. As previously described, the L shaped bracket 68 is fastened to the distal end 82 of the probe 48 and is held in a biased position by the spring 71. As can be ascertained, this causes the probe 48 to maintain a substantially constant tension in the first 52, second 54 and third 56 cables as the probe 48 is being advanced.

In addition, a feedback device (not shown) is coupled to the present invention. The feedback device determines a center point of reference for an ultrasonic beam emanating from the transducer 40. Prior to operation, the center point of reference is set. As the probe 48 is advanced during use, the feedback device continuously detects the transducer 40 position and determines whether it is facing substantially forward as desired. If the transducer 40 is not facing substantially forward, the feedback device increases or decreases the scanning motion as required in order to provide a new and corrected point of reference. Consequently, the center point of reference is continuously adjusted as the probe 48 is advanced. This enables the transducer 40 to provide a scan of the area or volume in front of the probe tip 42 as the probe 48 is advanced within an intravascular lumen or other internal cavity. The feedback device may include a light beam used in conjunction with optical markings on the ball 44 or transducer 40 which are utilized to determine orientation as will be described hereinafter.

Figure 6:
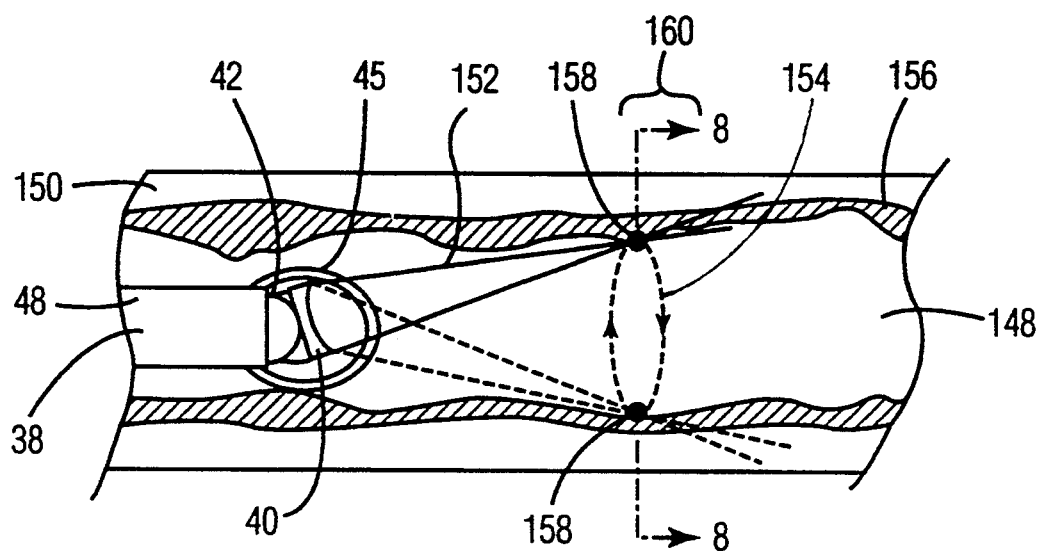
FIG. 6 shows an exploratory end of the present invention scanning a body lumen.
Figure 7:
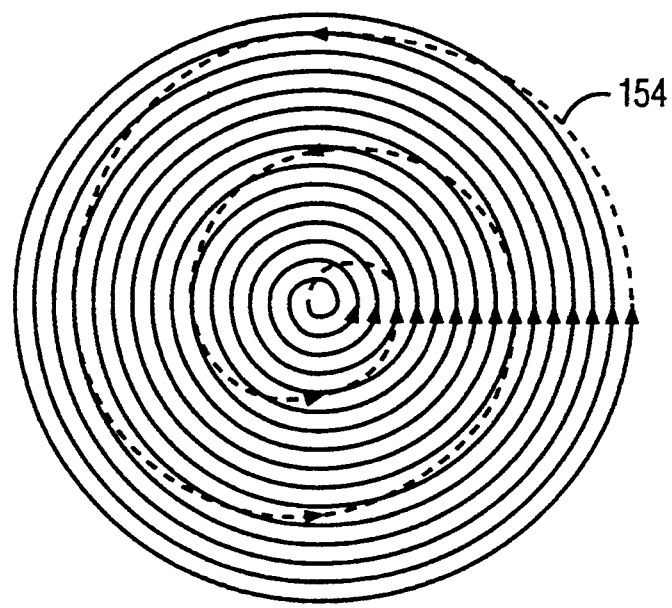
FIG. 7 depicts a spiral scan pattern produced by the displacements of FIGS. 5A and 5B.
Figure 8:
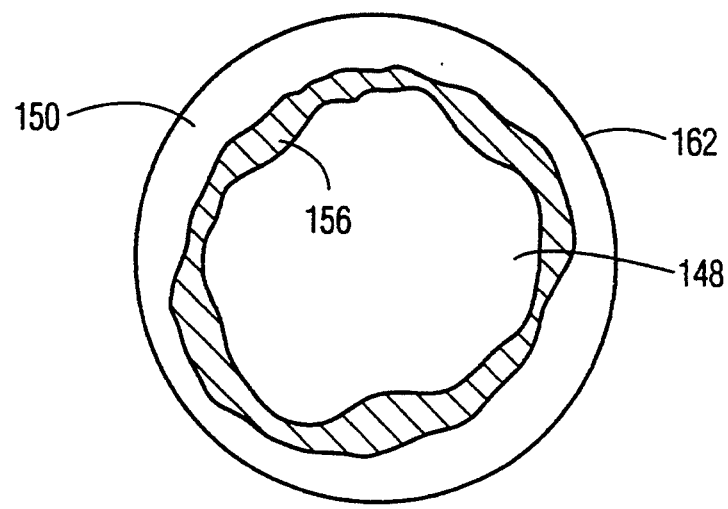
FIG. 8 shows an image of the body lumen scanned in FIG. 6.

Referring now to FIGS. 6–8 in conjunction with FIGS. 3 and 4, the scanning and imaging operation of the present invention apparatus can be described. In FIG. 6 the exploratory end 38 of the present invention probe 48 is shown scanning an oncoming area as it moves within a blood vessel 150. As has been previously described, the scanning pattern of the transducer 40 is dependent upon the displacement of the disc 76 by the first 118 and second 124 electromagnetic drivers. Although the scanning pattern can have any geometry, the preferred embodiment of the present invention has a scanning pattern 154 as shown in FIG. 7 that follows a descending and ascending spiral motion. In FIG. 7, the ascending spiral motions are shown as solid lines and the descending spiral motions are shown as dotted lines. Moreover, it can be ascertained that all scan rotations are in the same direction. The ascending spiral motion gradually increases and includes a plurality of turns while the descending spiral motion is relatively rapid. Moreover, data may be collected by the ultrasonic imaging system 144 during the ascending spiral motion which is then utilized to form an image on the display 146.

Referring to FIG. 6, the exploratory end 38 is positioned within a lumen 148 of a blood vessel 150. The blood vessel 150 is used by way of example only, and it is understood that other lumens or internal cavities can be scanned by utilizing the present invention. The transducer 40 emits an ultrasonic beam 152 in the manner previously described. The ultrasonic beam 152 emitted from the transducer 40 of the present invention will have a focal point 158. Therefore, the transducer 40 can be utilized within a focal zone 160. In order to provide a high resolution image, the portion of the area scanned that is in focus is recorded. The transducer 40 nutates in the spiral manner previously described. As a result, a spiral scan pattern 154 is produced (only one spiral motion is shown for clarity). The spiral scan pattern 154 is shown imaging material 156 within the lumen 148. The material 156 can be plaque or any other obstruction that may be found in the lumen 148.

The ultrasonic beam 152 is transmitted and received from the transducer 40 as the transducer 40 is cycled through its scanning pattern. The ultrasonic beam 152 is generated by the ultrasound imaging systems controller 144, electrically connected to the transducer 40 by the signal wire 58. Reflected ultrasonic beams are also received by the transducer 40 and are read by the ultrasound imaging systems controller 144, utilizing the same signal wire 58.

An image of an area can be obtained by emitting an ultrasonic beam and detecting its echo. Echo is generally known in the art as the reflection of an ultrasonic beam from the area or volume being scanned. The distance from the transducer 40 to the area being scanned corresponds to the round trip travel time for the ultrasonic beam 152 to travel from the transducer 40 and to return to the transducer 40. The image in the display 146 is then formed from the echoes of a plurality of spiral scanning patterns that arrive at the transducer 40 at a particular time. As the ultrasonic beam 152 scans a plane of interest, the returning echoes define that plane, which is known in the art as a "C" scan.

If the echoes of the plurality of scanning patterns are received and stored at various time intervals, the echoes describe several different planes that are at distances from the transducer 40 corresponding to their respective round trip travel times. By recording the signals received by the transducer 40 over the range in round trip travel times of ultrasonic beams within the focal zone 160, a plurality of image planes are provided by each spiral scan pattern 154. In addition, the image planes may be on either or both sides of the plane of interest.

This allows the ultrasonic imaging system 144 to provide multiple images over a depth or volume that may be shown in the display 146. In addition, the multiple image planes can be processed by the ultrasonic imaging system controller 144 to provide a volumetric, three dimensional image on the display 146 of the area or volume in front of the probe 48 as the probe 48 is advanced in the lumen or other internal cavity.

FIG. 8 is a view along section line 8—8 of FIG. 6. In FIG. 8, an image 162 is shown that is created by the scanning pattern set forth in FIG. 6. The image 162 is of the obstructing material 156 lining the blood vessel 150 in front of the transducer 40.

Figure 9:
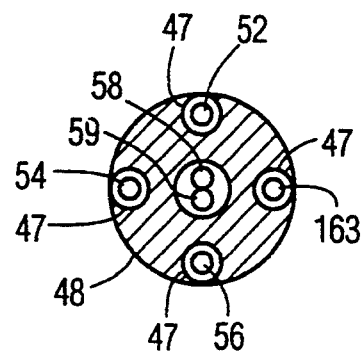
FIG. 9 is an alternate embodiment of the exploratory end employing four cables.

Referring to FIG. 9, an alternate embodiment of the present invention is disclosed. In FIG. 9, a cross section of the present invention probe 48 is shown containing four cables rather than the three cables previously described. Like numerals indicate like elements. A fourth cable 163, identical to the first 52, second 54 and third 56 cables, is added in the alternate embodiment, with each cable positioned in corresponding channels 47. The first 52, second 54, third 56 and fourth 163 cables are located in a circular arrangement and equally spaced. In addition, the first 52, second 54, third 56 and fourth 162 cables are fastened to the cable attachment plate 37 in the manner previously described and are symmetrically positioned around the plate 37. The signal wire 58 is located within the central hollow 64 of the probe 48 and is utilized in the manner previously described.

In the alternate embodiment, a fiber optic cable 59 is also positioned within the central hollow 64 and is coupled to the ultrasonic imaging controller 144. The ultrasonic imaging controller 144 provides a laser signal and the fiber optic element 59 is used to transmit the laser signal. The laser signal is used in conjunction with an optical marker which enables the ultrasonic imaging system 144 to detect the position of the ball 44 at the tip of the probe 48. To detect the position of the ball 44, the ball 44 may be encoded by means of a bar code or any other optical marker. This operates as a feedback control signal for the system to enable the accurate determination of transducer 40 orientation.

Figure 10A:
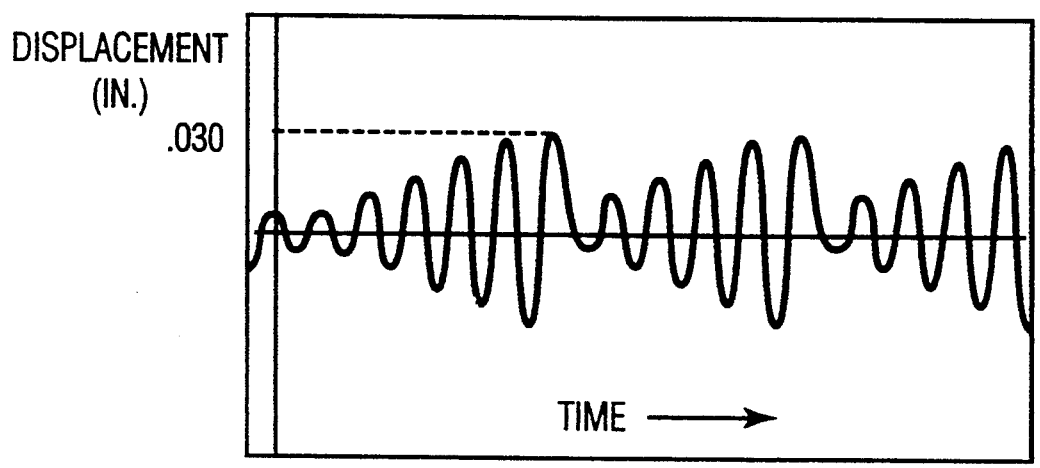
FIGS. 10A-10C show displacements as a function of time of each of three driveshafts of a present invention embodiment employing three electromagnetic drives.
Figure 10B:
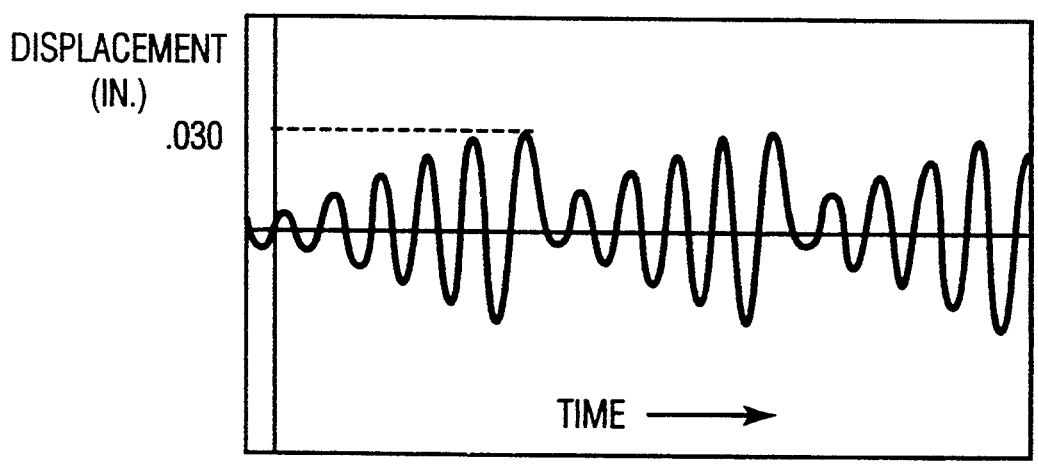
Figure 10C:
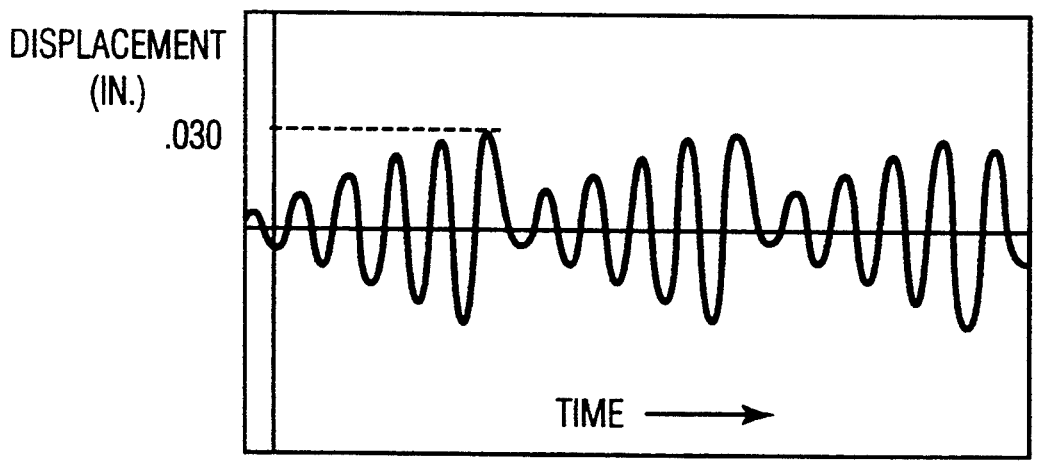

As can be readily understood by one of ordinary skill in the art, the present invention can be readily modified so as to add a third electromagnetic driver. A computer program can be employed that will cause the programmable power controller 144 to displace each output shaft of the electromagnetic drivers. Referring to FIGS. 10A-10C, a preferred vibration pattern is shown for each driveshaft of the three electromagnetic drivers. As can be seen, the sinusoidal displacements and the amplitudes are similar to those previously described. However, in the alternate embodiment, each driveshaft is 120 degrees out of phase instead of 90 degrees as in the preferred embodiment.

Figure 11A:
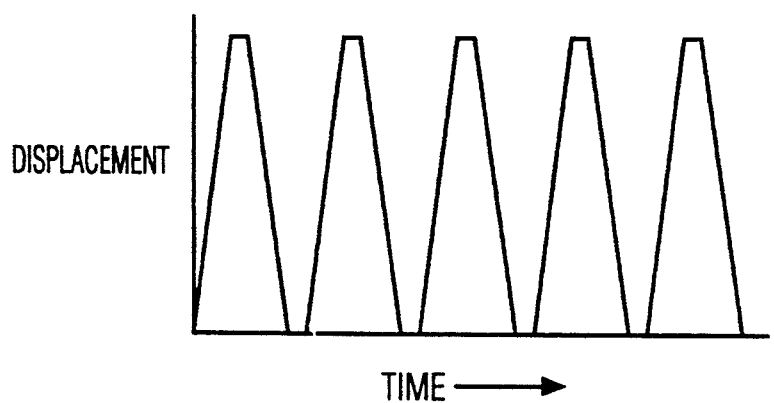
FIGS. 11A-11B show displacements as a function of time of each of four driveshafts of a present invention embodiment employing four electromagnetic drives.
Figure 11B:
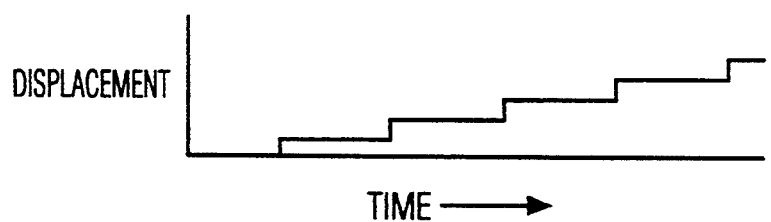
Figure 12:
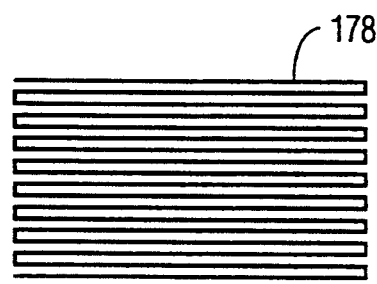
FIG. 12 depicts a raster scan pattern produced by the displacements of FIGS 11A-11B.

Moreover, a fourth electromagnetic driver may be added. FIG. 11A shows the resulting driveshaft displacement of two electromagnetic drivers as a function of time. FIG. 11B shows the driveshaft displacement of the other two electromagnetic drivers as a function of time. As can be readily understood, the resulting motion will nutate the transducer 40. FIG. 12 depicts a raster scanning pattern 178 produced by the driveshaft displacements depicted in FIGS. 11A and 11B.

Figure 13:
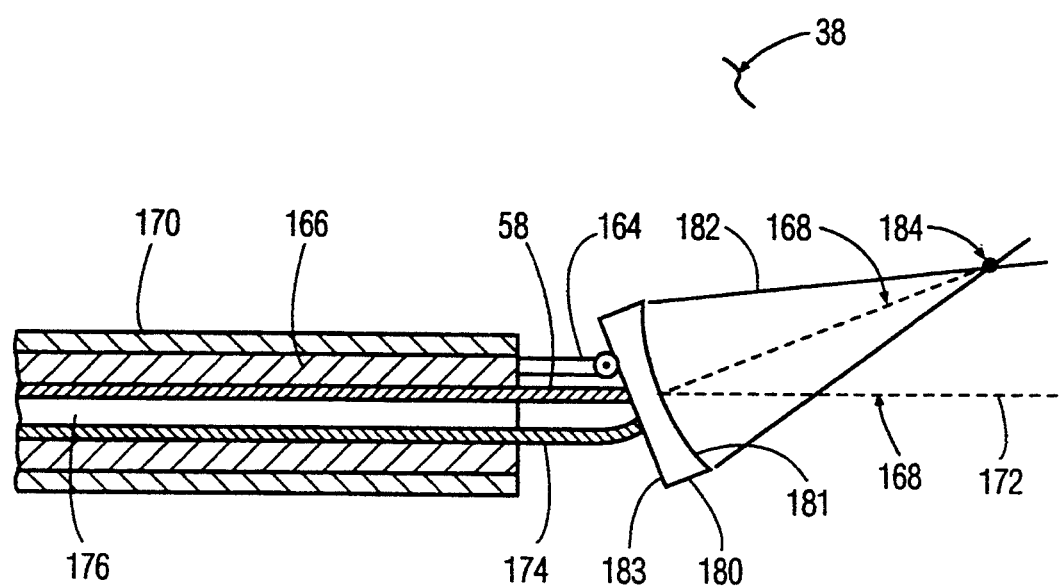
FIG. 13 is a present invention embodiment employing a hinged transducer.

FIG. 13 depicts a cross section of an alternate embodiment of the exploratory end 38. Like reference numerals indicate like elements. A transducer 180 having a forward facing concave head 181 and a flat rear surface 183 is positioned at a forward end of a hollow probe 170. The rear surface 183 is secured to an end of a hinge 164. An opposite end of the hinge 164 is fastened to an end of a hollow cylinder 166. The hollow cylinder 166 is positioned concentrically within the hollow probe 170 and is free to rotate within the hollow probe 170. The hollow cylinder 166 and hollow probe 170 have a central axis 172. An opposite end of the hollow cylinder 166 is coupled to a rotating means for rotating (not shown) the hollow cylinder 166. An end of the signal wire 58 is coupled to the transducer 180. The signal wire 58 extends through a hollow 176 within the hollow cylinder 166. An opposite end of the signal wire 58 is coupled to the ultrasonic imaging system 144 previously described. A flexible cable 174 is coupled to the rear surface 183. The cable 174 extends through the hollow 176 and is free moving within the hollow cylinder 166. An opposite end of the cable 174 is coupled to a moving means for moving (not shown) the cable 174. As is readily apparent to one of ordinary skill in the art, the present invention can be readily modified to provide the previously described rotating means and moving means. It is understood that the enclosure 45 previously described may be secured to the hollow probe 170 and utilized to encapsulate the transducer 180, hinge 164 signal wire 58 and cable 174.

In operation, the transducer 180 emits an ultrasonic beam 182 having a focal point 184 that forms an angle 168 with the central axis 172. The rotating means rotates the hollow cylinder 166 within the hollow probe 170. As a result, the transducer 180 nutates and produces a circular scan corresponding to the angle 168. The moving means moves the cable 174 relative to the hollow cylinder 166, thus changing the angle 168 as the hollow cylinder 166 rotates. By continuously changing the angle 168 from a minimum angle to a maximum angle as the transducer 180 nutates, a spiral scan pattern may be obtained.

What is claimed is:

1. A scanning system for ultrasonic imaging comprising:
   a catheter having a proximal and distal end;
   a transducer positionable at said distal end of said catheter;
   moving means coupled to said catheter to enable said catheter to move to a selected position along a given path; and
   mechanical scanning means coupled to said transducer for causing mechanical nutation of said transducer and to provide a conical scan substantially in front of said transducer and towards said selected position along said path according to said nutation.

2. A scanning system according to claim 1, wherein said scan includes an intraluminal area or volume substantially in front of said transducer.

3. A scanning system according to claim 1, wherein said scan includes a spiral scanning pattern to scan an area or volume in front of said transducer.

4. A scanning system according to claim 1, wherein said scan includes a raster scanning pattern to scan an area or volume in front of said transducer.

5. A scanning system according to claim 1, wherein said scanning means are coupled to a programmable controlling means for controlling said scanning means for providing a desired scan pattern to scan an area or volume in front of said transducer.

6. A scanning system according to claim 1, wherein said scanning means provides an ultrasonic signal to said transducer to cause said transducer to emit an ultrasonic beam.

7. A scanning system according to claim 1, wherein said moving means includes a probe for moving said transducer along said given path.

8. A scanning system according to claim 1, further comprising imaging means coupled to said transducer for providing images derived from said scan of said transducer.

9. A scanning system for ultrasonic imaging comprising:
  a probe for insertion into an intraluminal cavity, said probe having an exploratory end and an opposite end and disposed about a longitudinal axis:
  a transducer nutatably mounted to said exploratory end, said transducer comprising a relatively planar member;
  moving means coupled to said opposite end for moving said probe to a selected position along a given path;
  a plurality of cables having first and second ends, wherein said transducer is coupled to said first ends; and
  mechanical scanning means coupled to said second ends for causing said transducer to mechanically nutate in directions transverse to said longitudinal axis and provide a conical scan substantially in front of said transducer and towards said selected position along said path according to said nutation.

10. A scanning system according to claim 9, wherein said scanning means includes a plurality of electromagnetic drives that cause each of said plurality of cables to move to nutate said transducer.

11. A scanning system according to claim 9, further comprising a tension maintaining means for maintaining a constant tension in said plurality of cables.

12. A scanning system according to claim 9, wherein said scan of includes a raster scanning pattern to scan an area or volume in substantially front of said transducer.

13. A scanning system according to claim 9, wherein said scan includes a spiral scanning pattern to scan an area or volume substantially in front of said transducer.

14. A scanning system according to claim 9, wherein said scanning means are coupled to a programmable controlling means for controlling said scanning means for providing a desired scan pattern to scan an area or volume in front of said transducer.

15. A scanning system according to claim 9, wherein said scanning means provides an ultrasonic signal to said transducer to cause said transducer to emit an ultrasonic beam.

16. A scanning system according to claim 9, further comprising imaging means coupled to said transducer for providing images derived from said transducer of an area substantially in front of said transducer.

17. A scanning system for intraluminal imaging comprising:
  a transducer;
  moving means coupled to said transducer to enable said transducer to move to a selected position along a given path; and
  mechanical scanning means coupled to said transducer for causing said transducer to mechanically nutate and provide a conical scan of an area substantially in front of said transducer towards said selected position along said path according to said mechanical nutation.

18. A scanning system according to claim 17, wherein said scan of said oncoming area includes a spiral scanning pattern.

19. A scanning system according to claim 17, wherein said scanning means are coupled to a programmable controlling means for controlling said scanning means and providing said scan of said area.

20. A scanning system according to claim 17, wherein said scanning means provides an ultrasonic signal to said transducer to cause said transducer to emit an ultrasonic beam.

21. A scanning system according to claim 17, further comprising imaging means coupled to said transducer for providing images derived from said transducer of said area substantially in front of said transducer.

22. A scanning system for intraluminal imaging comprising:
  a probe having an exploratory end and an opposite end disposed about a longitudinal axis;
  a ball and socket assembly nutatably mounted to said exploratory end;
  a transducer mounted to said ball and socket assembly thereby enabling said transducer to nutate;
  moving means coupled to said opposite end for moving said probe to a selected position along a given path;
  a plurality of cables having first and second ends, wherein said ball and socket assembly is affixed to said first ends;
  driving means coupled to said second ends for mechanically driving said plurality of cables, thereby controlling the movement of said ball and socket and said transducer; and
  programmable controlling means coupled to said driving means for controlling said driving means and causing said transducer to mechanically nutate and provide a conical volumetric scan substantially in front of said transducer towards said selected position along said path according to said programmable controlling means.

23. A scanning system according to claim 22, wherein said scan of said oncoming area includes a raster scanning pattern.

24. A scanning system according to claim 22, wherein said scan of said oncoming area includes a spiral scanning pattern.

25. A scanning system according to claim 22, further comprising a tension maintaining means for maintaining a constant tension in said plurality of cables.

26. A scanning system according to claim 22, further comprising imaging means coupled to said transducer for providing images derived from said transducer of an area substantially in front of said transducer.

27. A scanning system according to claim 26, wherein said imaging means provides an ultrasonic signal to said transducer to cause said transducer to emit an ultrasonic beam.

28. A scanning system according to claim 26, further including a vibrating means, wherein said vibrating means includes a plurality of electromagnetic drives that cause each of said plurality of cables to move to nutate said transducer.

29. A scanning system according to claim 22, wherein said probe, said ball and socket, said transducer and said cables form an integral assembly that is removably secured to said driving means to enable disposal of said integral assembly after use.

30. A scanning system according to claim 22, further comprising a hollow enclosure fastened to said exploratory end for encapsulating said transducer, said plate and said first ends of said plurality of cables.

31. A method of intraluminal imaging, comprising the steps of:
  moving of a transducer to a selected position along a given path; and
  mechanically nutating said transducer to provide a conical volumetric scan of an intraluminal area in front of said transducer towards said selected position along said path.

* * * * *